US007311886B2

(12) United States Patent
Dumont D'Ayot et al.

(10) Patent No.: US 7,311,886 B2
(45) Date of Patent: Dec. 25, 2007

(54) CONTAINER CONTAINING AT LEAST TWO SOLID MATERIALS, AND USE THEREOF

(75) Inventors: Francois Dumont D'Ayot, Lyons (FR); Stephany Duplanil, Lyons (FR); Thomas Graf, St. Jean des Vigues (FR); Philippe Laffay, St. Foy les Lyon (FR); Thomas Wild, St. Wendel (FR)

(73) Assignee: Fresenius Medical Care Duetschland GmbH, Bad Homburg (DE)

( * ) Notice: Subject to any disclaimer, the term of this patent is extended or adjusted under 35 U.S.C. 154(b) by 0 days.

(21) Appl. No.: 10/498,004

(22) PCT Filed: Nov. 27, 2002

(86) PCT No.: PCT/EP02/13334

§ 371 (c)(1),
(2), (4) Date: Jun. 14, 2004

(87) PCT Pub. No.: WO03/053497

PCT Pub. Date: Jul. 3, 2003

(65) Prior Publication Data

US 2005/0031509 A1 Feb. 10, 2005

(30) Foreign Application Priority Data

Dec. 20, 2001 (DE) ................................ 101 62 959

(51) Int. Cl.
*B01D 61/00* (2006.01)

(52) U.S. Cl. ....................... 422/261; 422/102; 422/255

(58) Field of Classification Search ................ 422/102, 422/261, 255; 210/259, 257.1, 283, 284, 210/290, 291
See application file for complete search history.

(56) References Cited

U.S. PATENT DOCUMENTS

| | | | | |
|---|---|---|---|---|
| 3,307,736 | A * | 3/1967 | Kaplow | 220/231 |
| 3,669,880 | A | 6/1972 | Marantz et al. | |
| 5,217,854 | A * | 6/1993 | Abe | 430/465 |
| 5,326,473 | A * | 7/1994 | Lascombes et al. | 210/474 |
| 5,616,305 | A | 4/1997 | Mathieu | |
| 6,127,009 | A * | 10/2000 | Strassmann | 428/35.2 |
| 6,274,103 | B1 * | 8/2001 | Taylor | 422/261 |
| 6,407,070 | B1 * | 6/2002 | Kai et al. | 514/23 |
| 6,489,301 | B1 * | 12/2002 | Kobira et al. | 514/23 |

FOREIGN PATENT DOCUMENTS

| | | | |
|---|---|---|---|
| DE | 35 39 619 | C1 | 4/1987 |
| DE | 43 03 372 | A1 | 8/1994 |
| DE | 695 08 893 | T2 | 6/1996 |
| EP | 0 287 978 | A1 | 10/1988 |
| EP | 0 716 031 | A2 | 6/1996 |
| EP | 1 177 801 | A1 | 2/2002 |
| JP | 08092070 | A * | 4/1996 |
| JP | 08164198 | A * | 6/1996 |
| WO | WO 90/13323 | | 11/1990 |
| WO | WO 00/57833 | | 10/2000 |
| WO | WO 01/604 28 | A1 | 8/2001 |

OTHER PUBLICATIONS

Internet Publication: "Copy of Freeze Dried Ice-Cream used by Astronauts, 1983"; http://www.powerhousemuseum.com/collection/database/?irn=20101.*

Internet Publication: "What is Freeze Drying?"; http://www.wisegeek.com/what-is-freeze-drying.html.*

Internet Publication: "Astronaut Ice Cream"; http://everything2.com/index.pl?node_id=1204120.*

Takahashi Shuji, Solid Agent for Dialysis and Its Production, Jun. 30, 1997, vol. No. 06 (Abstract Only).

* cited by examiner

*Primary Examiner*—Gladys JP Corcoran
*Assistant Examiner*—Sean E. Conley
(74) *Attorney, Agent, or Firm*—Jacobson Holman PLLC

(57) ABSTRACT

This invention relates to a container having at least one inlet and/or outlet and containing at least two different solids arranged in layers as well as the use of said container for preparing a dialysate. In particular, a flexible bag is described, having three layers of different solids, where the middle layer consists of a solid which is compatible with the two adjacent layers and thus forms a separating layer between the two other layers. The layers are secured in place during shipping by vacuum packing.

10 Claims, No Drawings

CONTAINER CONTAINING AT LEAST TWO SOLID MATERIALS, AND USE THEREOF

This is a nationalization of PCT/EP02/13334 filed Nov. 27, 2002 and published in German.

This invention relates to a container having at least one inlet and/or outlet, said container containing at least two different solids arranged in layers as well as the use of said container for producing a liquid dialysate.

For treatment of a patient suffering from renal insufficiency, dialysis is performed to treat patients suffering from renal insufficiency. This is performed either in the peritoneum or through extracorporeal dialysis or filtration of blood. These two methods have in common the fact that dialysis fluids or dialysates take up the degradation products of metabolism. These dialysates usually contain high levels of sodium chloride and other electrolytes such as calcium chloride or potassium chloride, a buffer substance such as bicarbonate or acetate and acid to establish a physiological pH plus optionally glucose as an osmotic agent.

Dialysates are either supplied as ready-to-use solutions or they are prepared on site from concentrates, including solid concentrates. Solids offer the advantage of a small package volume and a low weight. Although solids also have disadvantages—electrolyte salts, for example, are highly hygroscopic—there is a trend toward offering only solid components for preparation of dialysates.

The solids are usually salts or crystals which may be in powder form or in granular form. European Patent EP 0 287 987 describes a granular mixture of the ionic components needed for preparation of a dialysate. German Patent DE 43 03 372 describes a bag for holding solid or liquid concentrate, usually of bicarbonate, which is used for preparing the dialysate and is connected directly to a dialysis machine.

Only components that will not react during their storage or otherwise influence one another through their chemical and/or physical properties, i.e., substances that are mutually compatible, are stored together in one container. Substances which under some circumstances can under some circumstances influence one another's chemical and/or physical properties are called incompatible substances. The lack of compatibility need not occur spontaneously but may also occur during a process to which the components are usually subjected, such as sterilization of dialysates.

To overcome this problem, separate storage has been preferred, whether in separate containers or containers having multiple compartments, so that the substances are mixed only shortly before the treatment. However, this results in other problems such as the problem of creating a connection system between the sterile containers or the individual containers of the dialysis machine, whether by joining key-and-lock connection systems that fit together, by breaking open a connecting channel or by tearing open a peelable seam. In addition, it is possible that the joining of the individual components may not be complete and/or only one of the components may be administered.

The object of the present invention is therefore to provide a container which avoids the disadvantages that have become known in the state of the art. This object is achieved through the features of the first claim.

Characteristic of this invention is the layered bed of at least two solids within a container. The solids should preferably be components for a dialysate and are in the form of a powder, crystals or granules, because the dialysate components are prepared from salts or glucose. The solids contained in it may be water-soluble but need not be. In the case of solids that are to form components of a dialysate, they are of course water-soluble. In addition, use of such a container for preparing a dialysate is thus also claimed.

If substances that are not compatible are used to fill the container, the layers must be arranged with a distance between them according to this invention. This may be accomplished either by a separation unit, e.g., a loose film or by another solid component. Preferably the incompatible components are separated from one another by a third component which is itself compatible with each of the two other components.

Compatible here is defined as not causing any mutual changes in their chemical and/or physical properties whereas incompatible or not compatible is defined conversely. This is understood to mean that the container is also exposed to extreme ambient conditions such as those prevailing during sterilization, for example, over a long storage time.

If two layers of incompatible solids are kept a distance apart by means of another solid, i.e., a third solid, then the latter may be in the form of small polymer beads, for example, which are themselves insoluble in water while the other solids are water-soluble. However, it is preferable for the third solid to be another component for producing a dialysate which then is especially preferably in the form of granules, powders or crystals and is also water-soluble.

Examples of components that are used for preparing the dialysate include electrolytes, acids, sodium chloride, sodium bicarbonate and glucose. Of the substances, sodium bicarbonate and glucose, for example, are not mutually compatible. Therefore, according to this invention, a layer of sodium chloride is placed between the layer of sodium bicarbonate and the layer of glucose.

Any type of solid cartridge or flexible bag is conceivable as the container; it should be made of a material that is also compatible with its ingredients. In the field of medical technology, in the past mainly solid cartridges made of polycarbonate or flexible bags made of polyvinylpyrrolidone have been provided for this purpose. However, these have been replaced to an increasing extent by polyolefins, especially polypropylene and polyethylene, in combination with synthetic rubbers. Special coatings which additionally provide a gas barrier or a water vapor barrier and offer special compatibilities or similar advantages are described in numerous variations in the state of the art.

The container should have at least one inlet to be able to fill it with the components. According to this invention, this inlet may also be used as an outlet at the same time. However, it is also conceivable for the inlets and outlets to be provided separately and/or for multiple inlets and/or outlets to be provided. These containers may also have connections, such as injection ports and ventilation and aeration devices or the like.

According to this invention, the solids are added to the container in layers. In order for the layers not to slip during storage, it is advantageous for the layers to be secured in place. It is conceivable here for a covering plate to be pressed onto the layers of solids and for such a plate to be lockable. However it is especially advantageous for unneeded gases or liquids to be removed from the container, e.g., by suction.

For this reason the preferred embodiment of this invention is a flexible bag in which a vacuum is created with the help of a pump after adding the solids layer by layer and which is then sealed airtight. It should be noted here that a space that is completely empty of air can never be formed, which is why the correct description refers to an interior space of the bag which contains the smallest possible amount of gas or fluid. Likewise, the embodiment as a flexible bag is not absolutely necessary but it is especially helpful if the solids contained in the bag are to be secured in place with the help of a "vacuum pack."

Securing the solids at their location inside the bag serves to prevent mixing of the solids so that incompatible solids cannot come in contact with each other. Although this invention is not limited to the use of solids for producing a dialysate, the preferred embodiment is nevertheless a flexible container which is filled with preferably all the substances required to prepare a dialysate, but at least is filled with solids that form a partial concentrate.

One conventional partial concentrate is prepared by using three substances, namely bicarbonate, sodium chloride and glucose. Glucose is subject to degradation when it comes in contact with an incompatible substance that has a basic pH, i.e., bicarbonate in this case. This is even more the case during hot steam sterilization. When two incompatible substances such as sodium bicarbonate and glucose as in this case are used for the partial concentrate, the especially preferred embodiment is a flexible bag having three layers of solids consisting of glucose, sodium chloride and sodium bicarbonate, with sodium chloride forming the middle layer and the layers being secured in place by suction removal of the air in the interior of the bag.

Such a filled bag is used for supplying the concentrate used to prepare the dialysate. It is especially advantageous if the amount present in the bag is just sufficient to prepare exactly the amount of dialysate necessary and sufficient for one dialysis.

The invention claimed is:

1. A combination container and composition for preparing a dialysate solution suitable for use in the treatment of kidney insufficiency, which comprises a container having at least one inlet or outlet, and three solids, each solid being in a powder, granular or crystalline form and being water-soluble, at least two of said solids being incompatible with one another and separated from one another by a layer of said third solid which is compatible with said at least two incompatible solids, each of solids being a component suitable for a dialysate solution used in the treatment of kidney insufficiency.

2. The combination container and composition according to claim 1, wherein the third solid is sodium chloride.

3. A combination container and composition for producing a dialysate solution suitable for use in the treatment of kidney insufficiency comprising:

a container having at least one inlet and one outlet;

a first solid and a second solid arranged in layers within said container;

each solid being in a powdered, granular or crystalline form, being water-soluble, and being a component suitable for a dialysate solution used in the treatment of kidney insufficiency; and when the first and second solids are incompatible with each other, said apparatus further including a third solid compatible with the first and second incompatible solids, said third solid also being in a powdered, granular or crystalline form, being water-soluble, and being a component suitable for a dialysate solution used in the treatment of kidney insufficiency, and disposed as a layer between the two incompatible solids.

4. The combination container and composition of claim 3 wherein said at least two solids are selected from the group consisting of electrolytes, acids, sodium chloride, sodium bicarbonate and glucose.

5. The combination container and composition of claim 3, wherein the third solid comprises sodium chloride.

6. The combination container and composition of claim 5, wherein the container includes a vacuum seal.

7. The combination container and composition of claim 5, wherein the container is flexible.

8. The combination container and composition of claim 5, wherein the container is a flexible bag formed of a polymer.

9. A combination container and composition for producing a dialysate solution suitable for use in the treatment of kidney insufficiency comprising:

a container having at least one inlet and one outlet;

a first solid and a second solid arranged in layers within said container;

each solid being in a powdered, granular or crystalline form, being water-soluble, and being a component suitable for a dialysate solution used in the treatment of kidney insufficiency;

said container includes a vacuum seal; and when the first and second solids are incompatible with each other, said apparatus further including a third solid compatible with the first and second incompatible solids, said third solid also being in a powdered, granular or crystalline form, being water-soluble, and being a component suitable for a dialysate solution used in the treatment of kidney insufficiency, and disposed as a layer between the two incompatible solids.

10. A combination container and composition for producing a dialysate solution suitable for use in the treatment of kidney insufficiency comprising:

a flexible bag made of a polymer forming a container having at least one inlet and one outlet;

at least a first solid and a second solid, each solid being in a powdered, granular or crystalline form and being a component suitable for a dialysate solution used in the treatment of kidney insufficiency, arranged in layers within said container, said solids being water-soluble and selected from the group consisting of electrolytes, acids, sodium chloride, sodium bicarbonate and glucose;

when said first and second solids are incompatible with each other, said apparatus further including sodium chloride in a powdered, granular or crystalline form disposed as a layer in between at least two incompatible solids; and said container further being vacuum sealed.

* * * * *